United States Patent [19]
Stark et al.

[11] Patent Number: 5,448,025
[45] Date of Patent: Sep. 5, 1995

[54] COVER FOR STETHOSCOPE HEAD

[76] Inventors: Wayne T. Stark, 4787 Yorkshire Way, Granite Bay, Calif. 95746; Raymond J. Mikelionis, 203 Grove St., Roseville, Calif. 95678

[21] Appl. No.: 276,896
[22] Filed: Jul. 19, 1994
[51] Int. Cl.⁶ ............................................. A61B 7/02
[52] U.S. Cl. ................................ 181/131; 181/137
[58] Field of Search ............... 181/131, 137; 128/715, 128/775, 798, 639; 381/67

[56] References Cited

U.S. PATENT DOCUMENTS

| | | | |
|---|---|---|---|
| 2,507,375 | 5/1950 | Hartwell et al. | 379/452 |
| 2,650,269 | 8/1953 | Webb | 379/452 |
| 2,651,380 | 9/1953 | Brandenburg | 181/131 |
| 3,213,960 | 10/1965 | Wagner | 181/131 |
| 3,255,841 | 6/1966 | Hasbrouck | 181/131 |
| 3,543,875 | 12/1970 | Littmann | 181/131 |
| 3,614,991 | 10/1971 | Machlup et al. | 181/131 |
| 3,867,925 | 2/1975 | Ersek | 181/131 |
| 4,461,368 | 7/1984 | Plourde | 181/131 |
| 4,867,265 | 9/1989 | Wright | 181/131 |
| 4,867,268 | 9/1989 | Ulert | 181/137 |
| 4,871,046 | 10/1989 | Turner | 181/131 |
| 5,054,063 | 10/1991 | Lo et al. | 379/452 |

Primary Examiner—Khanh Dang
Attorney, Agent, or Firm—Thomas R. Lampe

[57] ABSTRACT

A cover for temporary securement to a rigid stethoscope head to completely cover a diaphragm within the interior of the stethoscope head and seal the interior and the diaphragm from the ambient atmosphere. The cover includes a flat, double-sided, thin plastic sheet and a layer of adhesive on a side of the sheet to releasably sealingly secure the cover to the outer rim surface of a stethoscope head.

3 Claims, 1 Drawing Sheet

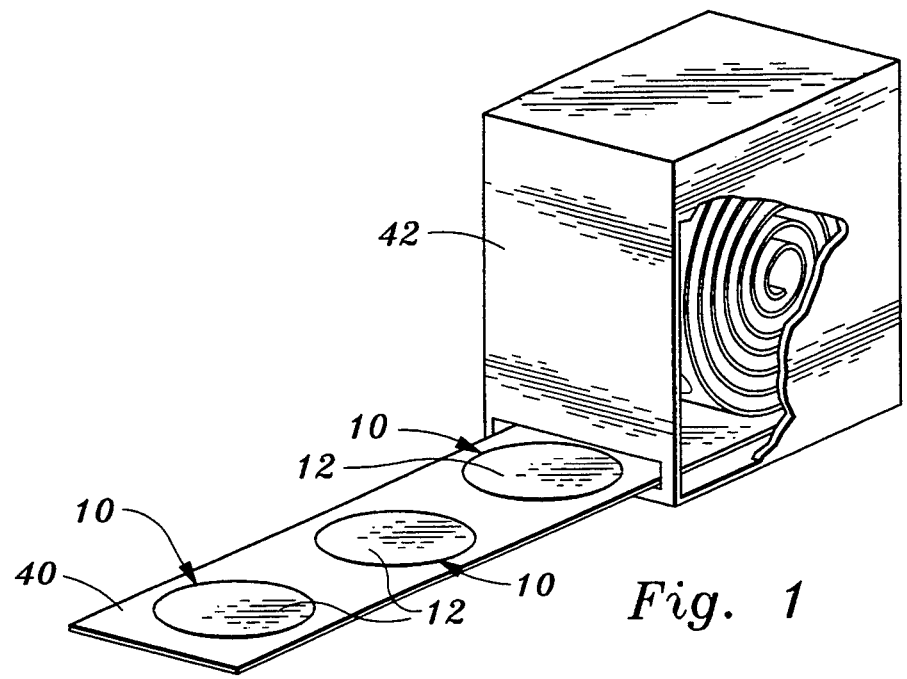
Fig. 1
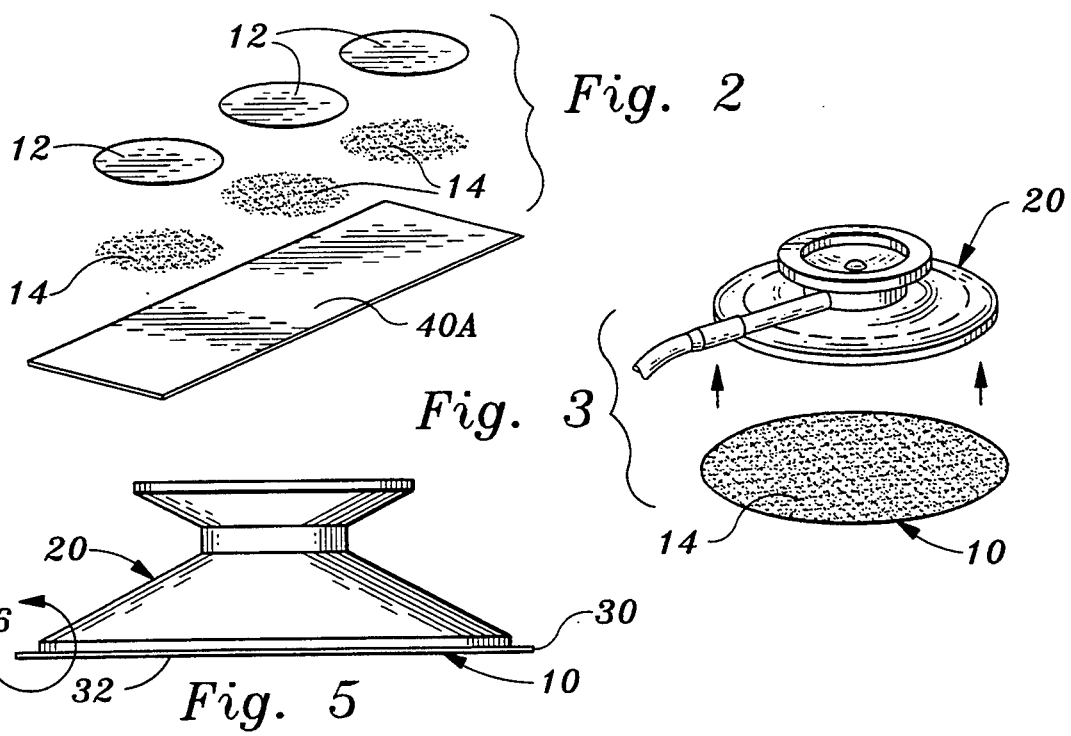
Fig. 2
Fig. 3
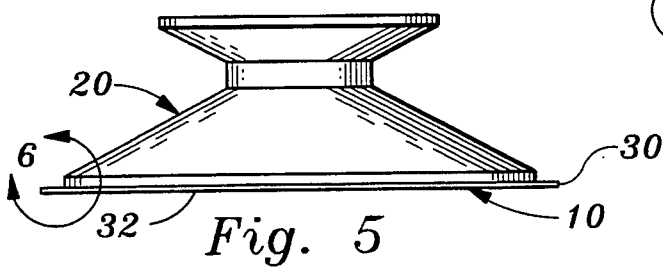
Fig. 5
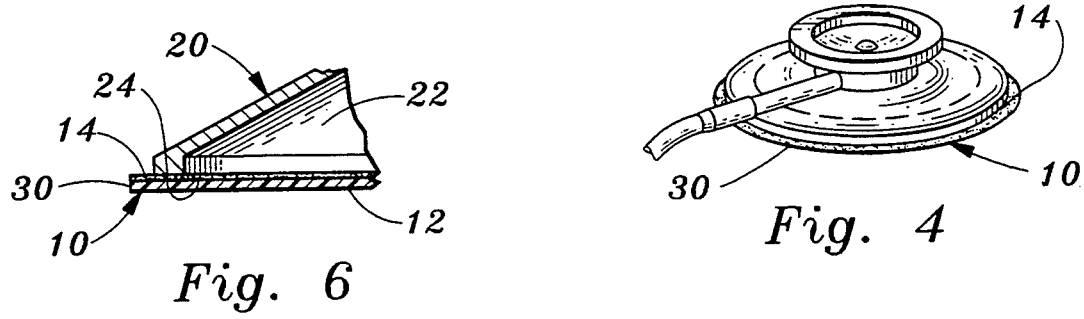
Fig. 6
Fig. 4

5,448,025

COVER FOR STETHOSCOPE HEAD

TECHNICAL FIELD

This invention relates to a cover for temporary securement to a rigid stethoscope head. The cover protects the stethoscope head from contamination during use. The cover does not impede the operation of the stethoscope.

BACKGROUND ART

A number of arrangements are known in the prior art which are for the purpose of protecting a stethoscope head against contamination. These prior art devices range from simple to complex.

U.S. Pat. No. 4,871,046, issued Oct. 3, 1989, discloses a disposable shield for stethoscope heads in the form of an envelope which is constructed from a single piece of plastic material in which the sides are folded toward each other, thereby defining two top portions overlaying a bottom portion. The edges are sealed as by heat sealing.

The disposable shield or cover of U.S. Pat. No. 4,871,046 is essentially in the form of an envelope which relatively loosely receives the stethoscope head. This approach allows excess material below, about and above the stethoscope head. This excess plastic sheet material can distort and move relative to the head when employed, thus creating extraneous sounds which adulterate and interfere with the sounds from the patient being transmitted to the stethoscope user.

U.S. Pat. No. 4,461,368, issued Jul. 24, 1984, discloses a cover for a stethoscope having a flexible membrane of latex and a rigid rim member. Such an arrangement is relatively complex and expensive and does not particularly lend itself to disposal and replacement after a single use. Furthermore, employment of several parts which must be secured together increases the likelihood of adulterating sounds and vibrations being introduced to the stethoscope.

Applicant is also aware of the following United States Patents which are believed to be further representative of the state of the prior art: U.S. Pat. No. 4,867,268, issued Sep. 19, 1989, U.S. Pat. No. 4,867,265, issued Sep. 19, 1989, U.S. Pat. No. 3,867,925, issued February 25, 1975, U.S. Pat. No. 3,614,991, issued Oct. 26, 1971, U.S. Pat. No. 3,543,875, issued Dec. 1, 1970, U.S. Pat. No. 3,255,841, issued Jun. 14, 1966, U.S. Pat. No. 3,213,960, issued Oct. 26, 1965, U.S. Pat. No. 2,651,380, issued Sep. 8, 1953, U.S. Pat. No. 5,054,063, issued Oct. 1, 1991, U.S. Pat. No. 2,650,269, issued Aug. 25, 1953, and U.S. Pat. No. 2,507,375, issued May 9, 1950.

DISCLOSURE OF INVENTION

The present invention relates to a cover for temporary securement to a rigid stethoscope head to completely cover a diaphragm within the interior of the stethoscope head and seal the interior and the diaphragm from the ambient atmosphere. The stethoscope head has a rim with an outer rim surface defining an opening leading to the interior.

The cover includes a flat, double-sided, thin plastic sheet and a layer of adhesive on a side of the thin plastic sheet for releasably bonding the cover to the outer rim surface of a stethoscope and forming a substantially air-tight seal between the cover and the stethoscope head.

The cover has an inner cover portion corresponding in size and configuration to the outer periphery of the outer rim surface and an outer cover portion surrounding and extending outwardly from the outer rim surface when the cover is releasably bonded to the outer rim surface whereby the outer rim surface, the stethoscope interior and the diaphragm are completely covered by the cover.

The preferred mode or embodiment of the invention utilizes a sheet of vinyl as the flat, double-sided, thin plastic sheet, the sheet of vinyl having a substantially uniform thickness in the range of from about 0.1 mil to about 0.4 mil.

Other features, advantages, and objects of the present invention will become apparent with reference to the following description and accompanying drawings.

BRIEF DESCRIPTION OF DRAWINGS

FIG. 1 is a perspective view of a dispenser device which may be utilized to dispense covers constructed in accordance with the teachings of the present invention;

FIG. 2 is an exploded, perspective view illustrating three covers, each including a plastic sheet component and an adhesive component, over a backing or carrier sheet;

FIG. 3 is a perspective view illustrating a cover being brought into engagement with a stethoscope head prior to securement thereto by the adhesive layer of the cover;

FIG. 4 is a view similar to FIG. 3 but illustrating the cover adhesively secured to the stethoscope head;

FIG. 5 is an enlarged side view of a stethoscope head illustrating the cover adhesively secured thereto; and FIG. 6 is an enlarged sectional view showing in detail the area delineated in FIG. 5 by double headed arrow 6.

BEST MODE FOR CARRYING OUT THE INVENTION

Referring now to the drawings, a cover constructed in accordance with the teachings of the present invention is designated by reference numeral 10.

Cover 10 includes a flat, double-sided, thin sheet of vinyl 12 having a layer of adhesive 14 covering a side thereof.

Vinyl sheet 12 has a substantially uniform thickness in the range of from about 0.1 mil to about 0.4 mil. It has been found that this specific material is highly suitable when practicing the teachings of the present invention. In particular, the vinyl sheet material within the indicated thickness range does not interfere with transmittal of unadulterated sound from patient to the stethoscope user. In fact, as noted below, sound transmittal is actually enhanced in many instances.

Any suitable adhesive may be utilized as adhesive layer 14. The adhesive should be characterized by uniformity of bonding, strength, and "ease of peel" which will allow for ready removal of the cover from the stethoscope head after use. The adhesive layer should be relatively thin so as not to interfere with the sound transmission capabilities of the stethoscope head. A laminate product sold under the trademark Clear-Ad by Catalina Plastics & Coating of Las Vegas, Nev. has been found appropriate for use when forming the cover of the present invention. The Clear-Ad product is conventionally used for advertisements temporarily applied to Windows and includes a vinyl layer and a thin layer of adhesive providing "ease of peel".

Cover 10 has a circular configuration and it has been found that a diameter of at least 2.25 inches allows the cover to be utilized with the vast majority of stethoscope heads currently on the market.

FIG. 3 shows a cover 10 being applied to a stethoscope head 20. As is conventional, the stethoscope head is rigid and has an interior 22 for accommodating a stethoscope diaphragm (not shown). Stethoscope head 20 has a rim with an outer rim surface 24 defining an opening leading to the stethoscope interior.

Application of a cover 10 to the stethoscope head is simplicity itself. The operator merely brings the adhesive layer 14 into contact with the outer rim surface 24 and presses the cover against the outer rim surface to bond the cover to the rim and form a seal which serves to seal both the interior and the diaphragm from the ambient atmosphere.

It will be noted that the cover is larger than the stethoscope head so that an outer cover portion 30 surrounds and extends outwardly from the outer rim surface. The inner cover portion 32 of the cover corresponds in size and configuration to the outer periphery of the outer rim surface.

The cover 10 not only covers the outer rim surface, the stethoscope interior and the diaphragm to protect the stethoscope head from contamination, but actually can improve sound transmission of a stethoscope with which it is operatively associated. Although the precise reason for this is not known with certainty, it is believed that sound transmission is enhanced by virtue of the fact that the cover seals any air leaks which might otherwise occur between the stethoscope diaphragm and the stethoscope head and rim. Furthermore, greater surface contact area exists between the cover and the patient than exists between the stethoscope head without the cover and a patient.

The cover may readily and quickly be removed from the stethoscope head after use by grasping the outer cover portion and peeling away the cover from the stethoscope head.

It is desirable to protect the layer of adhesive 14 from the air until just prior to actual use of the cover. FIG. 1 illustrates a plurality of covers 10 deployed on a carrier sheet 40 of waxed paper or the like. The carrier sheet 40 is configured in a roll and disposed in a dispenser carton 42. Of course, the carrier sheet may have other configurations. For example, FIG. 2 illustrates a carrier sheet 40A having a generally rectangular configuration and designed to accommodate three covers in side-by-side relationship. Another possibility is to employ a carrier or protector sheet having a configuration corresponding to the circular configuration of the cover.

We claim:

1. In combination:

a stethoscope including a rigid stethoscope head defining a stethoscope head interior for accommodating a stethoscope diaphragm, said stethoscope head having a rim with an outer rim surface defining an opening leading to the stethoscope head interior; and a cover of unitary construction releasably secured to said rigid stethoscope head completely covering the stethoscope interior and outer rim surface and completely sealing the stethoscope interior from the ambient atmosphere, said cover, wholly comprising a flat, double-sided, thin vinyl sheet and a thin layer of adhesive coated on one side of said thin vinyl sheet engaging the outer rim surface around the entire periphery of said stethoscope opening, releasably bonding said cover to the outer rim surface of said stethoscope and forming a substantially air-tight seal between said cover and the stethoscope head whereby the stethoscope interior is closed to the ambient atmosphere, said cover having an inner cover portion corresponding in size and configuration to the outer periphery of the outer rim surface and an outer cover portion surrounding and extending outwardly from the outer rim surface whereby said outer rim surface, the stethoscope interior and a stethoscope diaphragm accommodated within the stethoscope interior are completely covered by said cover, said sheet of vinyl having a substantially uniform thickness in the range of from about 0.1 mil to about 0.4 mil, and the side of the sheet of vinyl opposed to the adhesive coated side being free of adhesive to facilitate movement of the stethoscope head and cover to different locations on a patient's body.

2. The cover according to claim 1 wherein said cover has a circular configuration.

3. The cover according to claim 2 wherein said cover has a diameter of at least about 2.25 in.

* * * * *